(12) United States Patent
Miettinen et al.

(10) Patent No.: US 8,594,573 B2
(45) Date of Patent: Nov. 26, 2013

(54) SHORT RANGE WIRELESS COMMUNICATIONS

(75) Inventors: Jari Miettinen, Oulu (FI); Juhani Kemppainen, Oulu (FI)

(73) Assignee: Polar Electro Oy, Kempele (FI)

( * ) Notice: Subject to any disclaimer, the term of this patent is extended or adjusted under 35 U.S.C. 154(b) by 140 days.

(21) Appl. No.: 13/177,156

(22) Filed: Jul. 6, 2011

(65) Prior Publication Data

US 2012/0009875 A1 Jan. 12, 2012

(30) Foreign Application Priority Data

Jul. 9, 2010 (FI) .................................. 20105790

(51) Int. Cl.
*H04B 7/00* (2006.01)

(52) U.S. Cl.
USPC ........ 455/41.2; 455/231; 455/127.4; 370/478

(58) Field of Classification Search
USPC ............... 455/41.2, 231, 127.4, 171.1, 456.1; 370/478, 337
See application file for complete search history.

(56) References Cited

U.S. PATENT DOCUMENTS

| 5,611,346 | A | 3/1997 | Heikkila et al. |
| 6,816,724 | B1 * | 11/2004 | Asikainen .................. 455/414.1 |
| 6,950,668 | B2 * | 9/2005 | Brassil et al. .................. 455/517 |
| 7,020,474 | B2 * | 3/2006 | Scott ............................ 455/456.1 |
| 7,123,643 | B2 * | 10/2006 | Yamato .......................... 375/133 |
| 7,212,785 | B2 * | 5/2007 | Brassil et al. ................. 455/41.2 |
| 7,257,426 | B1 * | 8/2007 | Witkowski et al. ......... 455/569.2 |
| 7,483,682 | B2 * | 1/2009 | Williams .................... 455/180.1 |
| 7,684,375 | B2 * | 3/2010 | Gurin ............................ 370/338 |
| 7,773,635 | B2 * | 8/2010 | Eichinger et al. ............. 370/478 |
| 8,078,109 | B1 * | 12/2011 | Mulcay ......................... 455/63.1 |
| 8,179,805 | B2 * | 5/2012 | Singh et al. ................... 370/242 |
| 8,213,874 | B2 * | 7/2012 | Agnew ....................... 455/67.13 |
| 8,238,831 | B2 * | 8/2012 | Sen ............................... 455/63.1 |
| 2004/0093380 | A1 * | 5/2004 | Sellen et al. .................. 709/204 |
| 2006/0143455 | A1 * | 6/2006 | Gitzinger ..................... 713/170 |
| 2007/0202807 | A1 | 8/2007 | Kim |
| 2009/0062778 | A1 | 3/2009 | Bengtsson et al. |
| 2009/0111378 | A1 | 4/2009 | Sheynman et al. |
| 2009/0182388 | A1 | 7/2009 | Von Arx et al. |
| 2009/0270949 | A1 | 10/2009 | Kalpin et al. |
| 2009/0280745 | A1 | 11/2009 | Granqvist et al. |

FOREIGN PATENT DOCUMENTS

| EP | 2107837 A1 | 10/2009 |
| EP | 2335563 A1 | 6/2011 |
| WO | WO2008059460 A2 | 5/2008 |

OTHER PUBLICATIONS

Tomi Koskinen, Finnish Search Report for corresponding Finnish Application No. 20105790, p. 1 (May 2, 2011).
Yves Vanderperren, European Search Report for corresponding European Application No. EP11172320, pp. 1-4 (Oct. 28, 2011).

* cited by examiner

*Primary Examiner* — Minh D Dao
(74) *Attorney, Agent, or Firm* — Hoffmann & Baron, LLP

(57) ABSTRACT

This document presents a wireless communication scheme utilizing a combination of two wireless communication schemes: a short range communication scheme and a radio communication scheme having a longer wireless transmission range than the wireless transmission range of the short range communication scheme. A short range signal is used to indicate a radio resource to be used for transmitting a radio signal, and the radio signal is then communicated in the radio resource indicated by the short range signal.

19 Claims, 3 Drawing Sheets

SHORT RANGE WIRELESS COMMUNICATIONS

CROSS-REFERENCE TO RELATED APPLICATION

This application claims priority based on Finnish Application No. 20105790, filed Jul. 9, 2010, which is incorporated herein by reference.

BACKGROUND

1. Field

The invention relates to the field of wireless short range communications.

2. Description of the Related Art

A transmitter apparatus, such as a heart rate monitor, may communicate information, such as heart activity data, to a receiver apparatus, such as an exercise apparatus, over a wireless link. However, as there may be many transmitter apparatuses present in a gym, for example, it may be problematic to find out which transmitter apparatus wishes to be paired together with a specific receiver apparatus or which pair of a transmitter apparatus and a receiver apparatus should communicate with each other.

SUMMARY

According to an aspect of the present invention, there is provided an apparatus comprising a transmission control circuitry configured to control a short-range transmitter and a radio transmitter operationally connectable to the transmission control circuitry, the radio transmitter having a longer wireless transmission range than a wireless transmission range of the short-range transmitter, wherein the transmission control circuitry is configured to cause the short-range transmitter to transmit a short-range signal indicating to a receiver apparatus receiving the short-range signal a radio resource used for transmission of a radio signal, and to cause the radio transmitter to transmit the radio signal in the radio resource indicated with the short-range signal.

According to another aspect of the present invention, there is provided a method comprising: causing, in a wireless communication apparatus, communication of a short-range signal indicating a radio resource used for transmission of a radio signal, wherein the radio signal has a longer wireless communication range than a wireless communication range of the short-range signal; and causing, in the wireless communication apparatus communication of the radio signal in the radio resource indicated with the short-range signal.

According to another aspect of the present invention, there is provided an apparatus comprising means for carrying out the above-mentioned method.

According to yet another aspect of the present invention, there is provided a computer program product embodied on a non-transitory distribution medium readable by a computer and comprising program instructions which, when loaded into the computer, execute a computer process comprising: causing, in a wireless communication apparatus, communication of a short-range signal indicating a radio resource used for transmission of a radio signal, wherein the radio signal has a longer wireless communication range than a wireless communication range of the short-range signal, and causing, in the wireless communication apparatus communication of the radio signal in the radio resource indicated with the short-range signal.

According to an aspect, there is provided an apparatus comprising a reception control circuitry configured to control a short-range receiver and a radio receiver both operationally connectable to the reception control circuitry. The reception control circuitry is configured to detect reception of a short-range signal in the short-range receiver, to determine from the received short-range signal a radio resource of a radio signal, and to cause the radio receiver to receive the radio signal in the radio resource determined from the short-range signal and to decode data carried by received radio signal.

In an embodiment, the radio resource indicated with the short-range signal is a reception timing of the radio signal, and the reception control circuitry is arranged to synchronize the radio reception circuitry to receive the radio signal at the reception timing determined from the received short-range signal.

In an embodiment, the reception timing of the short-range signal indicates the reception timing of the radio signal.

In an embodiment, the short-range signal is a measurement signal carrying information on a measurement, and the reception control circuitry is arranged to receive short range signals at irregular time intervals.

In an embodiment, the measurement signal is a heart-rate signal and the receiver apparatus is an exercise apparatus configured to process the measurement signal and to provide information on an exercise on the basis of the processed measurement signal.

In an embodiment, the radio signal carries an identification code that identifies a radio transmitter that transmitted the radio signal, and the reception control circuitry is arranged to identify the radio transmitter from the identification code received in the radio signal associated with the radio resource indicated by the received short range signal and to configure the radio receiver to execute a pairing protocol for a radio connection with said radio transmitter.

In an embodiment, the short-range receiver is an induction-based receiver and the short range signal is a magnetic signal.

In an embodiment, the reception control circuitry is arranged to compare a reception timing of a radio signal received through the radio receiver with a reception timing of the short-range signal and to decode the radio signal, if the reception timing of the radio signal relative to the reception timing of the short-range signal matches with a predetermined timing relation.

Further embodiments of the invention are defined in the dependent claims.

BRIEF DESCRIPTION OF THE DRAWINGS

Embodiments of the present invention are described below, by way of example only, with reference to the accompanying drawings, in which.

DETAILED DESCRIPTION

The following embodiments are exemplary. Although the specification may refer to "an", "one", or "some" embodiment(s) in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned.

Figure 1:
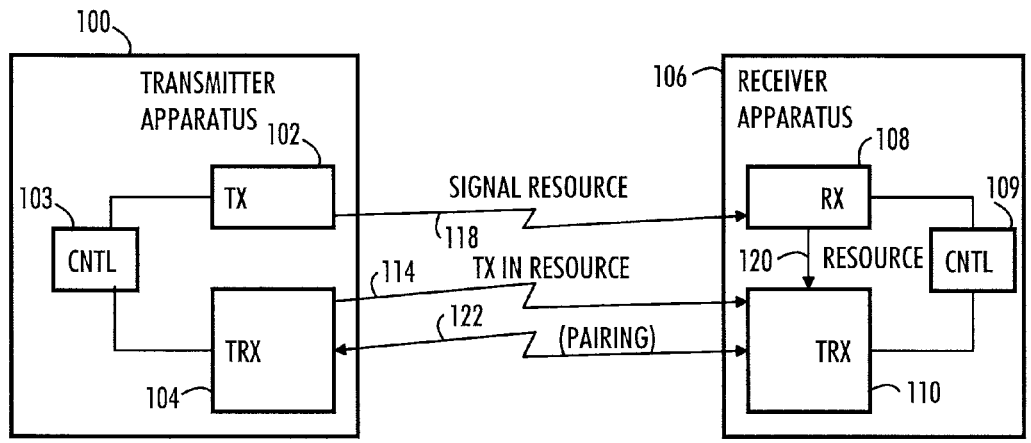
FIG. 1 illustrates block diagrams of devices according to embodiments of the invention.

FIG. 1 illustrates a transmitter apparatus 100 and a receiver apparatus 106. FIG. 1 is a simplified block diagram that only shows some elements and functional entities, all being logical units whose implementation may differ from what is shown. The connections shown in FIG. 1 are logical connections; the actual physical connections may be different. It is apparent to a person skilled in the art that the described apparatuses 100, 106 may also comprise other functions and structures, e.g. a memory and/or a user interface. It should be appreciated that some functions, structures, and elements, and the actual protocols used for communication may vary in different embodiments of the invention. Therefore, they need not be discussed in more detail here. The specifications of apparatuses 100, 106 develop rapidly. Such a development may require extra changes to the described embodiments. Therefore, all words and expressions should be interpreted broadly and they are intended to illustrate, not to restrict, the embodiments. Although the apparatuses 100, 106 have been depicted as separate single entities, different parts may be implemented in one or more physical or logical entities.

The term 'transmitter apparatus' 100 may refer to a complete device that a user is capable of carrying around, or to a part of such a device. The complete device 100 may be a heart rate monitor, a heart rate transmitter wearable on the chest of a user, or another personal measurement device, for example a positioning device, a stride sensor or a blood pressure monitor. A part of such a device 100 may be an electronic circuitry implementing or causing the implementation of the described functionalities of the transmitter apparatus 100. The electronic circuit may comprise one or more digital signal processors configurable by software, logic components, standard integrated circuits, and/or application-specific integrated circuits (ASIC).

The term 'receiver apparatus' 106 may refer to a complete device capable of interacting with the transmitter apparatus 100, or to a part of such a device. The complete device 106 may be a computer, a wearable exercise apparatus, e.g. a wrist computer, a portable computer, a mobile phone, or a health club apparatus, for example. A part of such a device 106 may be an electronic circuit implementing or causing the implementation of the described functionalities of the receiver apparatus 106. The computer may be a personal computer such as a desktop computer, a laptop computer, or a palmtop computer. The computer may also be a server computer. The computer may store and process heart activity data of numerous persons. The computer may be team-specific, i.e. it is used to process the heart activity data of a certain team. Alternatively, the computer may provide heart activity data storage and analysis services to a wide audience, as a worldwide web (WWW) server over the Internet, for example. If the receiver apparatus 106 is an exercise apparatus, such as a treadmill, the training load may be regulated, a diary may be stored, etc. by utilizing the communication to be described later on.

The transmitter apparatus 100 comprises a wireless transmission circuitry comprising two communication devices: a short range transmitter 102 and a radio transmitter 104, wherein at least one of the short range transmitter 102 and the radio transmitter 104 may be provided with reception functionalities as well. The short range transmitter 102 and the radio transmitter 104 may be provided as separate logical and physical entities realized by separate circuits comprised in the wireless transmission circuitry, or they may be physically in the same circuit. The short range transmitter 102 may comprise a digital to analog converter converting a digital transmission signal into analog waveforms, and an analog transmission circuitry including at least one amplifier arranged to amplify the analog transmission signal, at least one filter filtering the analog transmission signal to mitigate undesired signal components, optionally at least one frequency converter configured to frequency-convert the transmission signal, and an antenna radiating the transmission signal into an air interface. In an embodiment, the antenna is typically based on a coil structure enabling inductive signal transmission used in the short-range transmission.

The radio transmitter 104 may comprise a digital-to-analog converter converting a digital transmission signal into analog waveforms, and an analog transmission circuitry including at least one amplifier arranged to amplify the analog transmission signal, at least one filter filtering the analog transmission signal to mitigate undesired signal components, at least one frequency converter configured to frequency-convert the transmission signal into a radio frequency, and an antenna radiating the transmission signal into an air interface. The antenna may be different from the antenna comprised in the short range transmitter 102. When the radio transmitter 104 is equipped with reception capabilities, the radio transmitter 104 is a radio transceiver comprising a reception circuitry including said radio antenna, at least one amplifier arranged to amplify an analog reception signal received through the antenna, at least one filter filtering the analog reception signal to mitigate undesired signal components, at least one frequency converter configured to frequency-convert the reception signal from the radio frequency into a baseband or to an intermediate frequency, and an analog-to-digital converter converting the analog reception signal into a digital form for digital signal processing and data recovery.

The receiver apparatus 106 comprises a wireless reception circuitry comprising a short range receiver 108 and a radio receiver 110, wherein at least one of the short range receiver 108 and the radio receiver 110 may be provided with transmission functionalities as well. The short range receiver 108 and the radio receiver 110 may be provided as separate logical and physical entities realized by separate circuits comprised in the wireless reception circuitry, or they may be physically in the same circuit. The short range receiver 108 may comprise an analog reception circuitry including an antenna and at least one amplifier arranged to amplify an analog reception signal received through the antenna, at least one filter filtering the analog reception signal to mitigate undesired signal components, optionally at least one frequency converter configured to frequency-convert the reception signal to the baseband, and an analog-to-digital converter converting the analog reception signal into a digital form for digital signal processing and data recovery. In an embodiment, the antenna is typically based on a coil structure enabling a reception of magnetic signal.

The short-range signal transmission and reception are described in detail in U.S. Pat. No. 5,611,346, which is hereby incorporated as reference. The short-range signal, such as that based on inductive transmission, may include identification structures, such as sub-pulses, which can be used for associating the short-range signal with an ad-hoc measurement, such as a heart rate measurement. Thus, each short-range signal can be received independent on each other at any time instant and identified correctly.

The radio receiver 110 may comprise an analog reception circuitry including a radio antenna, at least one amplifier arranged to amplify an analog reception signal received through the radio antenna, at least one filter filtering the analog reception signal to mitigate undesired signal components, at least one frequency converter configured to frequency-convert the reception signal from the radio frequency into a baseband or to an intermediate frequency, and an analog-to-digital converter converting the analog reception signal into a digital form for digital signal processing and data recovery. When the radio receiver 110 is equipped with transmission capabilities, the radio receiver 110 is a radio transceiver comprising additionally a digital-to-analog converter converting a digital transmission signal into analog waveforms, and an analog transmission circuitry including at least one amplifier arranged to amplify the analog transmission signal, at least one filter filtering the analog transmission signal to mitigate undesired signal components, at least one frequency converter configured to frequency-convert the transmission signal into the radio frequency, and said radio antenna radiating the transmission signal into the air interface.

In an embodiment, the radio communication devices 104 and 110 are configured to provide a bidirectional radio communication link. To define the short range communication devices 102, 108, their wireless communication range (or a coverage area) is shorter than the wireless communication range of the radio communication devices 104, 110. The short range communication devices 102 and 108 may be configured to utilize a communication method based on magnetic induction, and the induction-based transmitters are used in the embodiments described herein. However, the short range communication devices 102 and 108 may alternatively use another wireless communication method having a short communication range, e.g. radio transmission where the communication is based on near-field radio transmissions in a near field of radio frequency antennas, and a near field communication (NFC) technology.

In the embodiments of the present invention, two different wireless communication technologies are used: a short range communication technology utilizing a magnetic field, for example, and a radio-based technology utilizing electric (radio frequency) radiation. A difference between these two communication technologies is that the short range communication technology has a shorter wireless communication range than the radio communication technology. In other words, the difference between the two wireless communication technologies is signal attenuation as a function of the length of a signal propagation path. When using the induction-based communication technology as the short range communication technology, the signal level is inversely proportional to the third power of the length of the signal propagation path, whereas in a typical radio-based technology, the signal level is inversely proportional to the second power of the length of the signal propagation path. A typical coverage of the induction-based communication is of the order of human dimensions, i.e. about 1.5 meters. This results in a dramatic difference in the wireless communication range. This property causes that in a typical environment, e.g. a gym, a room, or outdoors, the receiver apparatus may receive numerous radio transmissions but only a single short range transmission, and this fact may be used to recognize the transmitter apparatus 100 with which the receiver apparatus 106 should communicate.

The short range transmitter 102 may be a kilohertz-range inductive transmitter, a passive radio-frequency identification tag, or a NFC transmitter, for example. Correspondingly, the short range receiver 108 may be a kilohertz-range inductive receiver, a radio-frequency identification tag reader, or a NFC receiver, for example. The kilohertz-range transmission may operate at 5-kilohertz frequency, for example. Higher frequencies, such as those exceeding 200 kilohertz, may also be possible. In an embodiment, the kilohertz-range includes 125 kilohertz. NFC as a term may refer to a short-range high frequency wireless communication technology which enables communication over about a 10-centimeter distance.

The radio transceiver 104, 110 may be a proprietary transceiver, or a Bluetooth transceiver, for example. Emerging ultra low power Bluetooth technology may be used, as its expected use cases include heart rate monitoring. The proprietary radio transmission may operate at 2.4-gigahertz frequency, for example.

The transmitter apparatus 100 further comprises a transmission control circuitry 103 configured to control the transmissions in the short range transmission circuitry 102 and in the radio transmission circuitry 102. Similarly, the receiver apparatus 106 further comprises a reception control circuitry 109 configured to control the short range reception circuitry 102 and the radio reception circuitry 102. The communication control circuitries 103, 109 may be realized by one or more digital signal processors configurable by one or more computer programs stored in one or more memory units accessible by the communication control circuitries 103, 109, or they may be ASIC (Application-Specific Integrated Circuit) implementations. Functionalities of the communication control circuitries 103, 109 may be distributed to the transmission/reception circuitries 102, 104, 108, 110, or dedicated control circuitries 103, 109 as shown in FIG. 1 may be provided.

According to an embodiment of the invention, the transmission control circuitry 103 is configured to cause, i.e. control, the short-range transmitter 102 to transmit a short-range signal 118 indicating to the receiver apparatus 106 a radio resource used for transmission of a radio signal 114. Then, the transmission control circuitry 103 causes, i.e. controls, the radio transmitter 104 to transmit the radio signal 114 in the radio resource indicated with the short-range signal 118. In the receiver apparatus 106, the reception control circuitry 109 is configured to detect reception of the short-range signal 118 in the short-range receiver, to determine from the received short-range signal 118 the radio resource 120 for the radio signal 114, and to control the radio receiver 108 to receive the radio signal 114 in the radio resource 120 determined from the short-range signal 118 and to decode data carried by received radio signal 114.

In practice, the short-range communication signal 118 is used to identify the transmitter apparatus 100 so as to enable the receiver apparatus 106 to receive and decode a correct radio signal 114. As mentioned above, the receiver apparatus 106 may receive numerous radio signals from different transmitter apparatuses but, typically, it receives a single or only a few short range signals 118 because of the short wireless communication range of the short range signal 118. In any case, the number of short range signals received by the receiver apparatus 106 is less than the number of radio signals received by the receiver apparatus 106, which speeds up recognition of the correct transmitter apparatus 100. In an embodiment, the radio signal 114 transmitted in the radio resource indicated by the short range signal 118 is a Bluetooth inquiry signal used in a pairing procedure 122 of a Bluetooth connection, and the receiver apparatus 106 may detect the correct inquiry signal on the basis of the short range signal indicating in which radio resource the inquiry signal is received. Accordingly, the pairing procedure 122 is facilitated. Upon completion of the pairing procedure, information may be exchanged 124 between the transmitter 100 and receiver 106 apparatuses over the established Bluetooth connection.

In an embodiment, the radio transceiver 104, 110 is a Bluetooth-based transceiver, such as Bluetooth Low Energy (BLE).

In an embodiment, the radio transceiver 104, 110 is an ANT transceiver originally introduced by Dynastream Innovations.

In an embodiment, the radio transceiver 104, 110 is a Zigbee transceiver based on IEEE 802.15.4 standard or its derivative.

In an embodiment, the radio transceiver 104, 110 is a WiFi transceiver based on IEEE 802.11x standard.

In an embodiment of the invention, the radio transceiver 104, 110 comprises at least two transceivers selected from the group comprising: Bluetooth or its derivatives, ANT or its derivatives, Zigbee or its derivatives, WiFi or its derivatives.

Figure 2A:
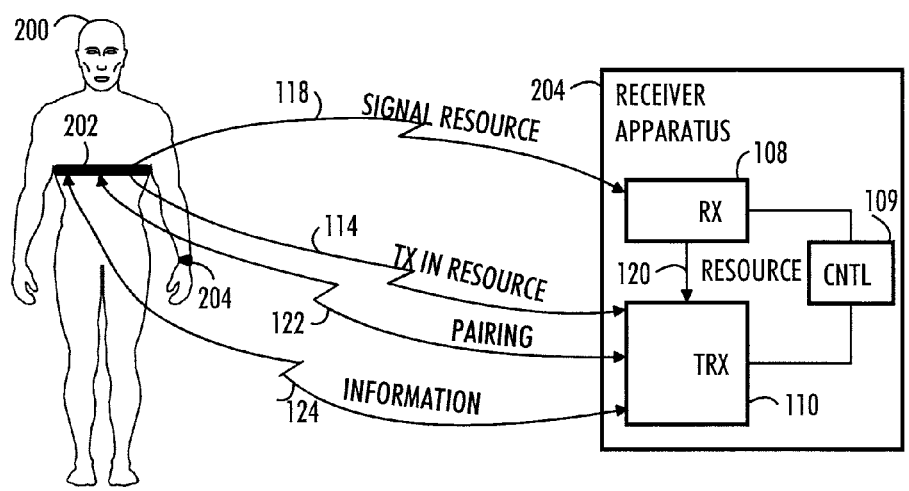
FIGS. 2A and 2B illustrate communication modes according to embodiments of the invention.
Figure 2B:
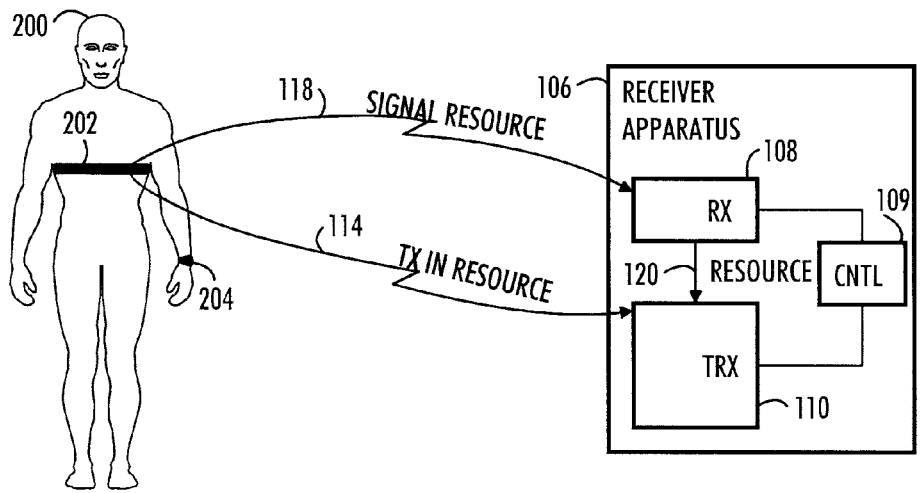

FIGS. 2A and 2B illustrate embodiments describing the wireless communication between the transmitter and receiver apparatuses 100, 106 in two operational environments. The transmitter apparatus 100 and the receiver apparatus 106 together form a wireless communication system according to an embodiment of the invention.

Referring to FIG. 2A let us consider a scenario where the transmitter apparatus 100 is a heart rate transmitter 202 worn by the user 200, and the receiver apparatus 106 is another personal exercise apparatus 204 also worn by the user. In this example, the receiver apparatus 106 is a wrist computer 204. As both apparatuses 202, 204 are carried by the user, the apparatuses 202, 204 may be configured to pair with each other so as to transfer data over the radio communication link, e.g. a Bluetooth link. In order to enable the wrist computer 204 to identify the heart rate transmitter 202 in an initial pairing, for example, the short range communication link 118 is used. Accordingly, the transmission control circuitry 103 of the heart rate transmitter 202 causes the short range transmitter 102 of the heart rate transmitter 202 to transmit a short range signal 118 comprising information on a radio resource in which the radio signal will be transmitted from the heart rate transmitter 202. The radio resource indicated by the short range signal 118 may include at least one of the following: a time resource (reception time instant and optionally duration of a reception time window), frequency resource (a radio channel/frequency index), a spreading code resource, a frequency hopping pattern index (particularly for Bluetooth), or any other radio resource used for transmitting the radio signal. Additionally, the short range signal may carry an identification code of the transmitter apparatus, e.g. a MAC (Medium Access Control) address. The short range signal 118 may carry a plurality of different types of above-mentioned radio resource information, e.g. a frequency channel index and a transmission timing of the radio signal. The information on the radio resource may be encoded into the short range signal 118, and the short range signal 118 may carry the radio resource index in its waveform structure.

In an embodiment where the radio resource is the time resource, duration or offset between transmission timings of the short range signal 118 and the radio signal 114 may be fixed and, thus, the short range signal 118 inherently indicates the transmission timing for the radio signal 114 without needing to carry any data encoded into the waveform of the short range signal 118. In other words, the transmission timing of the short range signal 118 indicates the radio resource of the radio signal 114 in such an embodiment.

The short range receiver circuitry 108 of the wrist computer 204 detects the short range signal 118 transmitted by the transmitter apparatus. The reception control circuitry 109 determines the radio resource from the received short range signal 118. Then, the reception control circuitry 109 tunes the radio receiver circuitry 110 to receive in the determined radio resource. When the determined radio resource is a time resource, the reception control circuitry 109 configures the radio receiver to receive the radio signal 114 at the determined timing. When the determined radio resource is a time resource, the reception control circuitry 109 configures the radio receiver to tune into the determined frequency and/or adapt to a determined frequency-hopping pattern. When the determined radio resource is a spreading code resource, the reception control circuitry 109 configures a correlator of the radio receiver monitor for a spreading code sequence determined from the received short range signal. Similarly, the reception control circuitry 109 configures the radio receiver for other types of radio resources determined from the short range signal.

The transmission control circuitry 103 of the heart rate transmitter 202 then causes the radio transmitter 104 to carry out the radio transmission 114 in the radio resource indicated in the short range signal 118, and the radio receiver 110 of the wrist computer 204 tuned by the reception control circuitry 109 to the radio resource 120 is able to receive the radio transmission 114 on the basis of the information determined from the received short range signal 118. The transmitted radio signal 114 may contain an identification code of the radio transmitter 104 and/or any control information used in a pairing procedure. As a consequence, the wrist computer 204 is able to execute the pairing procedure 122, wherein the pairing may include exchange of information 122 between the radio transceiver circuitries of the heart rate transmitter 202 and the wrist computer 204. Upon completion of the pairing 122, heart rate information or other information may be transmitted 124 from the heart rate transmitter 202 to the wrist computer 204 over the paired radio link. Such information may then be displayed or played back to the user 200 through the user interface of the wrist computer 204. The user interface of the wrist computer may comprise a display, a loudspeaker, a keypad comprising one or more buttons, a touch sensitive display, etc. Control information 124 configuring the operation of the heart rate transmitter 202 may be transmitted from the wrist computer 204 to the heart rate transmitter 202.

In the embodiment of FIG. 2A, the short range transmitter 102 and the short range receiver 108 may be switched off upon completed pairing so as to reduce power consumption. Accordingly, in response to detecting completed pairing for the radio connection, the transmission control circuitry 103 is configured to cause the shutdown of the short range transmitter 102. Similarly, in response to detecting completed pairing for the radio connection, the reception control circuitry 109 is configured to cause the shutdown of the short range receiver 108.

In an embodiment, the reception control circuitry 109 of the receiver apparatus 106 is configured to shut down the radio receiver 110 and activate it upon detection of the short range signal 118 and tuning the radio receiver to the radio resource determined from the short range signal. Upon reception of the radio signal 114 in the radio resource, the reception control circuitry 109 may again shut down the radio receiver 110 to reduce power consumption of the receiver apparatus 106. This embodiment is especially useful, when the receiver apparatus 204 is battery-operated.

In the embodiment of FIG. 2B, the transmitter apparatus 100 is the heart rate transmitter 202, and the receiver apparatus 106 may be an exercise apparatus, such as a treadmill, an exercise bike, a rowing machine, or a cross trainer provided at a gym.

In an embodiment, the receiver apparatus 106 is comprised in an exercise computer of an exercise apparatus. In this embodiment, the short range transmitter of the heart rate transmitter 202 is controlled by the transmission control circuitry 103 to transmit the short range signal 118 indicating the radio resource for the radio signal 114, as described above.

In an embodiment, the heart rate information is transmitted in the radio signal 114 in the radio resource indicated by the short range signal 118. In this case, the heart rate transmitter 202 is configured to transmit payload data, such as heart rate information in the radio signal 114 and in the radio resource indicated by the short range signal 118. The radio transmitter may be configured to operate in a connectionless advertising mode, for example. The transmission control circuitry 103 of the heart rate transmitter 202 causes its wireless transmission circuitry to transmit repeatedly a signal sequence comprising first the short range signal 118 indicating the radio resource for the radio signal 114 and, thereafter, the radio signal 114 carrying the payload data in the radio resource indicated by the short range signal 118. Upon reception of the short range signal(s) 118 through the short range receiver 108, the reception control circuitry 109 tunes its radio receiver 110 to the radio resource(s) determined from the short range signal(s) 118 and receives and decodes the payload data from the radio signals 114 received by the radio receiver 110 in the determined radio resources. The decoded payload data may then be further processed and displayed to the user.

In an embodiment, the reception control circuitry 109 is configured to maintain the radio receiver 110 active all the time and tune the radio receiver 110 to the radio resource determined from the received short range signal. This embodiment may be applied to cases, where the receiver apparatus 110 is connected to mains and when there is practically limitless power supply.

In the embodiment of FIG. 2A, the transmission of the measurement data, e.g. heart rate information, may be communicated in a connected state upon establishment of the paired connection, while in the embodiment of FIG. 2B, the measurement data may be transmitted in a connectionless state, e.g. when the transmitter apparatus is in an advertising state. In order to support both operation environments of FIGS. 2A and 2B, the transmitter apparatus 202 may be configured to transmit the payload data as described in connection with FIG. 2B until the pairing procedure is triggered or completed. As a consequence, the communication mode according to the embodiment of FIG. 2B is enabled by default, and the communication mode may be switched to the communication mode of the embodiment of FIG. 2A upon completion of the pairing procedure. Then, the transmitter apparatus 100, 202 may be configured to carry out the transmission of the payload data without indicating the radio resources in the short range signal, as the radio signal may carry an identifier of the transmitter apparatus 100, 202 enabling the identification of the correct transmitter, or the correct transmitter apparatus may be determined in another manner without the short range signals, e.g. through radio communications synchronized between the transmitter 202 and the receiver 204, 106.

The embodiment of FIG. 2B may also be used when the receiver apparatus 106 is the wrist computer 204 or another personal exercise apparatus. The communication mode of FIG. 2B may be triggered by disconnection and failed reestablishment of the paired link. In other words, when the paired radio connection is terminated abruptly, i.e. in an uncontrolled manner, the transmission control circuitry 103 of the transmitter apparatus 100, 202 detects the disconnection and configures the short range transmitter 102 to start transmit the short range signal indicating the radio resource for the transmitted radio signal and the radio transmitter 104 to transmit the heart rate information (or another information) in the radio resource. Similarly, the reception control circuitry 109 of the receiver apparatus 106, 204 detects the disconnection and configures the short range receiver 108 to receive short range signals, determine the radio resources from the received short range signals, and tune the radio receiver 110 receive the radio signals in the radio resources. As a consequence, upon failed radio connection, the communication may be continued in a connectionless communication mode where the short range link is used to point out the radio resources in which the radio communication is carried out. In an embodiment, the radio transmissions carry the payload data in the connectionless mode. In another embodiment, the transmitter apparatus 100, 202 buffers the payload data upon disconnection, controls the radio transmitter 104 to transmit pairing data in the radio resources until the new pairing is successfully completed and, then, starts transmitting the data stored in the buffers.

It should be noted that both the embodiments of FIGS. 2A and 2B are both applicable to any implementation of the receiver apparatus 106, 204. In other words, the embodiment of FIG. 2B may be used when the receiver apparatus 106, 204 is comprised in a personal exercise apparatus, and the embodiment of FIG. 2A may be used when the receiver apparatus 106, 204 is comprised in a non-personal exercise apparatus.

Figure 3:
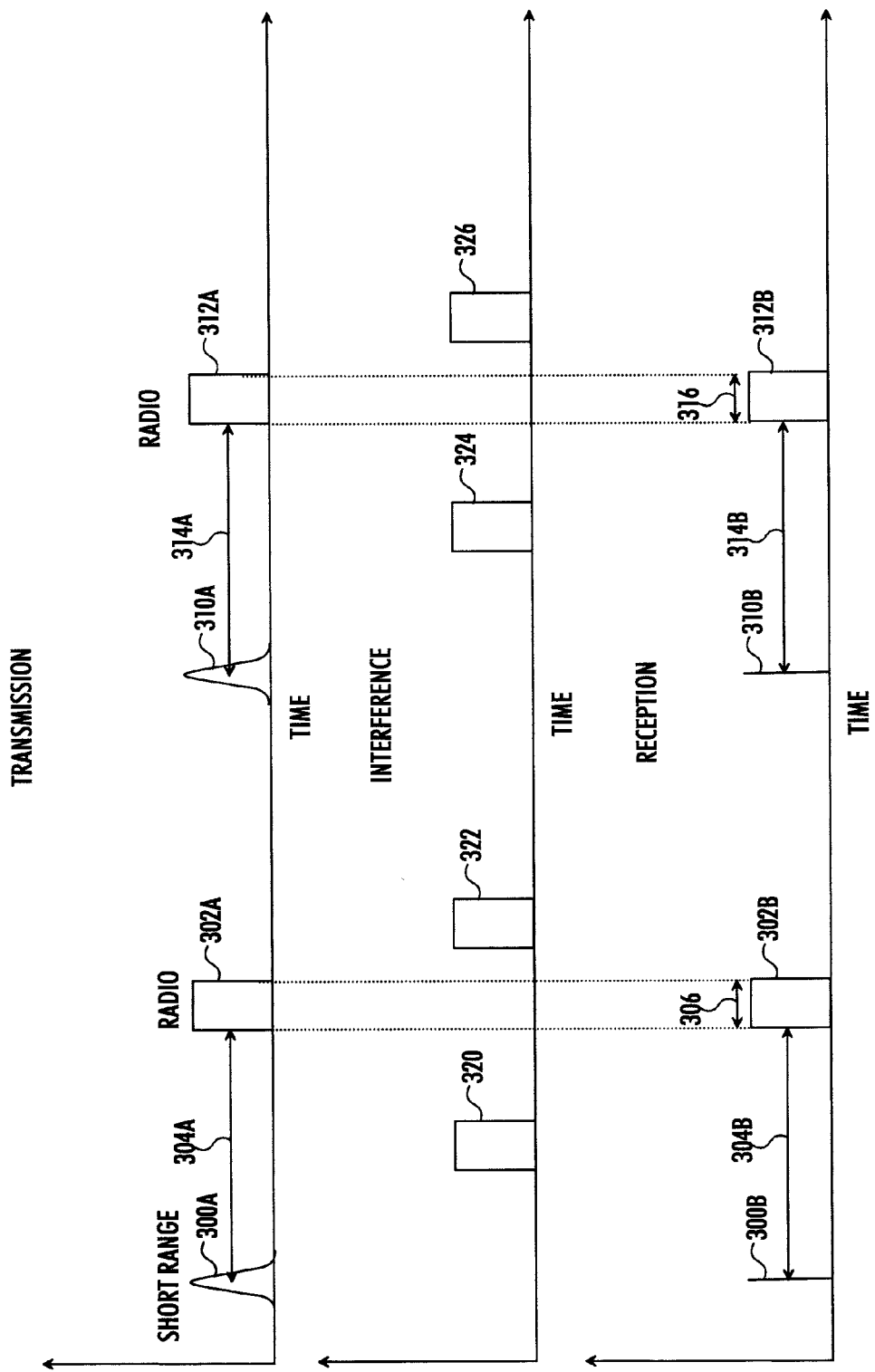
FIG. 3 illustrates time diagrams related to wireless communication according to an embodiment of the invention.

FIG. 3 illustrates physical layer communication in an embodiment where the radio resource indicated with the short range signal is a time resource. In more detail, a time between the transmission of the short range signal and the transmission of the radio signal is fixed, i.e. the transmission timing of the short range signal indicates the transmission timing of the radio signal. Similarly for the receiver apparatus 106, 204, a reception timing of the short range signal triggers the reception timing for the reception of the radio signal. In the three graphs of FIG. 3, the horizontal axis denotes time and the vertical axis denotes amplitude or another metric proportional to the signal power. The upmost graph illustrates transmissions of the short range and radio signals from the transmitter apparatus 100, 202, the middle graph illustrates interference, i.e. radio transmissions of other transmitter apparatuses that may be received by the receiver apparatus 106, 204, and the bottom graph illustrates the actual reception of the receiver apparatus 106, 204. Referring to the topmost graph, the transmission control circuitry 103 of the transmitter apparatus 100, 202 causes the short range transmitter 102 to transmit a first short range signal 300A at a given transmission timing from its short range transmitter. As the time interval 304A between the transmission timings of the short range signal and the radio signal is fixed, e.g. 100 ms, the transmission control circuitry 103 waits for the fixed time duration and, then, causes the radio transmitter 104 to transmit a first radio signal 302A.

As seen from the middle and the bottom graphs of FIG. 3, the receiver apparatus 106, 204 may receive two other radio transmissions 320, 322 quite close to the first radio signal 302A, and it should determine which one of the signals is transmitted by the correct transmitter apparatus 100, 202. The short range receiver of the receiver apparatus 106, 204 receives the short range signal 300B from the transmitter apparatus 100, 202 and, as the fixed time interval between the timings 304B of the short range signal and the radio signal is known also to the reception control circuitry 109 of the receiver apparatus 106, 204, the reception control circuitry 109 of the receiver apparatus 106, 204 configures its radio receiver 110 to receive the first radio signal in a time interval 306, wherein at least the start time for the radio reception is computed from the reception timing of the short range signal 300B by adding the known fixed time interval 304B to it. In this embodiment, the reception control circuitry 109 may comprise or be connected to a timer to count the fixed time duration from the detection of the reception of the short range signal.

In an embodiment, the reception control circuitry 109 of the receiver apparatus 106, 204 activates the radio receiver 110 to receive on a physical layer for the duration of the first radio signal 302A, i.e. for the duration of the time interval 306 and, upon expiry of the time interval 306, the reception control circuitry 109 deactivates the radio receiver to save power. The duration 306 may include guard periods so that the actual duration 306 starts before the radio signal 302A, 312B and ends after the radio signal 302A, 312A. The duration of a guard time may vary from microseconds to tens of milliseconds.

In another embodiment, the reception control circuitry 109 keeps radio receiver of the receiver apparatus active all the time, i.e. it receives all the radio signals 320, 322, 302B. Then, the reception control circuitry 109 may determine which one of the radio signals is received at the correct time instant 304B after the reception of the first short range signal 300B. As the interference signals 320, 322 are received either too early (signal 320) or too late (signal 322) with respect to the reception timing of the first short range signal 300B, they are discarded, and the radio signal 302B received after the determined time interval 304B after the reception of the first short range signal 300B is selected for decoding.

Similarly, the transmission control circuitry may cause the short range transmitter 104 to transmit a second short range signal 310A, wait for the fixed time duration 314A and, then, transmit a second radio signal 312A. Again, the receiver apparatus 106, 204 may be able to receive also interfering radio transmissions 324, 326, but on the basis of the reception timing of the short range signal 310B and the known time interval 314B between the reception timing of the short range signal 310B and the radio signal 312B, the reception control circuitry 109 is able to configure its radio receiver 110 to receive the radio signal during the appropriate time interval 316 and to decode a correct radio signal.

In the embodiment of FIG. 3, the radio resource indicated with the short range signal is timing. Then, the radio receiver 110 may be configured to scan, at the determined reception timing, all the frequencies known to be used by a radio protocol the radio receiver 110 supports. The same applies to other radio resources that are not indicated with the short range signal but that are used for transmitting the radio signal, i.e. the radio receiver 110 may be configured to scan all or some of the frequency-hopping patterns, spreading code sequences etc. possibly used by the radio transmitter 104. The more different types of radio resources are indicated by the short range signal, the less resources need to be scanned by the radio receiver 110.

Figure 5:
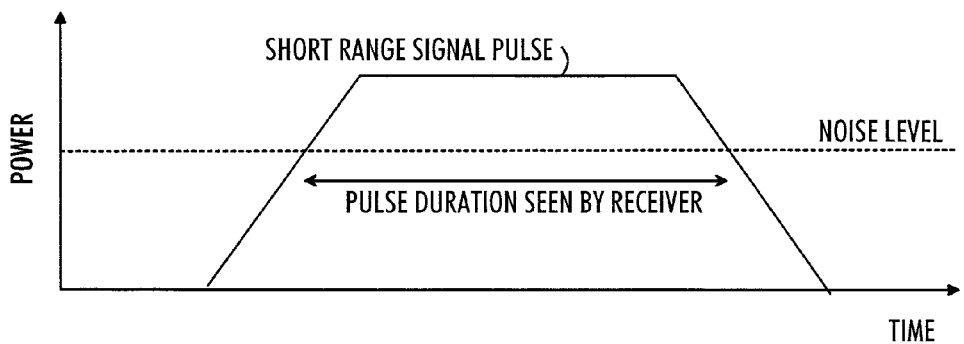
FIG. 5 illustrates an example of a short range signal pulse that may be used in connection with embodiments of the invention.

When there are multiple transmitter apparatuses 100, 202 according to embodiments of the present invention close to the receiver apparatus 106, 204, the receiver apparatus 106, 204 may receive multiple short range signals. In such a case, the strong attenuation of the short range signal may be used to determine the transmitter apparatus 100, 202 that is closest to the receiver apparatus 106, 204. FIG. 5 illustrates an example of a short range signal pulse. As conventional, the short range signal pulse comprises a rising edge, a peak edge, and a fall time, as illustrated in FIG. 5. FIG. 5 illustrates also a noise level. The closer the transmitter apparatus is to the receiver apparatus 106, 204, the stronger is the signal pulse with respect to the noise level (the noise level is on a lower level in FIG. 5), and the longer is the pulse duration seen by the receiver apparatus 106, 204. Similarly, the greater is the distance between the transmitter apparatus and the receiver apparatus 106, 204, the weaker is the signal pulse with respect to the noise level (the noise level is on a higher level in FIG. 5), and the shorter is the pulse duration seen by the receiver apparatus 106, 204. In other words, the shorter is the distance between the transmitter and the receiver, the more the receiver receives the rising and falling edges of the short range signal pulse. For example, for a 5 kHz inductive transmission of 5 ms duration, the receiver sees the pulse to have 5 to 8 ms duration, depending on the distance between the transmitter and the receiver (5 ms to the shorter distance and 8 ms to the longer distance). According to an embodiment, the reception control circuitry 109 of the receiver apparatus 106, 204 may determine the correct transmitter apparatus by computing the pulse duration for every short range signal received by the short range receiver 108, and select the short range signal that is determined to have the largest pulse duration. Then, the reception control circuitry 109 of the receiver apparatus 106, 204 is configured to determine the radio resource from the selected short range signal and tune the radio receiver 110 to that radio resource.

When the radio resource is encoded as an index into the pulse duration, the reception control circuitry 109 may compare the pulse duration of the received short range signal with reference lengths denoting the radio resource indices and determine the difference between the pulse duration of the received short range signal and the radio resource index it indicates. Then, the short range signal having the highest difference with respect to the radio resource index it indicates is selected as the correct short range signal. For example, let us consider a case where a frequency channel 37 is denoted by pulse duration of 9 ms, frequency channel 38 is denoted by pulse duration of 13 ms, and frequency channel 39 is denoted by pulse duration of 17 ms. The receiver may see the 9 ms transmission as having duration between 9 and 12 ms, 13 ms transmission as having duration between 13 and 16 ms, and 17 ms transmission as having duration between 17 and 20 ms. For example, if the short range receiver 108 of the receiver apparatus 106, 204 receives an 18 ms pulse and a 15 ms pulse, the reception control circuitry 109 may select channel 38 for the radio reception, because the 15 ms pulse is 2 ms longer than the reference duration (15 ms−13 ms=2 ms), while the 18 ms pulse is only 1 ms longer than the reference duration (18 ms−17 ms=1 ms), thereby indicating that the transmitter apparatus transmitting the 18 ms pulse has a greater distance to the receiver apparatus 106, 204 than the transmitter apparatus transmitting the 15 ms pulse. Accordingly, the reception control circuitry 109 tunes its radio receiver to channel 38 to receive the payload data and/or pairing information.

When the radio resource indicated by the short range signal is a time resource, when the time duration between the short range signal and the radio signal is fixed, and when a plurality of transmitter apparatuses close to the receiver apparatus 106, 204 are arranged to transmit the signals periodically with the same periodic cycle, it is possible that the two transmissions collide. As mentioned above, in an embodiment the transmitter apparatus is a measurement apparatus (the heart rate transmitter) comprising a measurement processing circuitry configured to execute measurement signal processing. According to an embodiment, the transmission of the short range signal is triggered by occurrence of a determined event in the measurement. When the event in the measurement occurs irregularly, it inherently induces the same irregularity to the transmission of the short range signal and, thus, avoids continued collisions between two (or more) transmitter apparatuses. When the measurement apparatus is a biometric sensor, e.g. the heart rate transmitter described above, the triggering event may be detection of a determined event in biometric measurement data. For example, when the measurement apparatus is the heart rate measurement apparatus, the determined event in the biometric measurement data may be the detection of an R waveform (or another waveform) in a measured ECG (electrocardiogram) signal. Detection of the R waveform triggers the transmission control circuitry 103 to cause the short range transmitter 102 to transmit the short range signal indicating the radio resource. Meanwhile, the measurement processing circuitry may process the measured signal by computing at least one of the following parameters: cardiovascular data such as heart rate information, heart beat interval (e.g. RR interval) heart rate variability data, energy expenditure data. Then, the computed parameters are encoded for radio transmission and transmitted from the radio transmitter 104 in the radio resource indicated in the short range signal. The receiver apparatus 106, 204 receives the parameters from the radio transmission, as described above, decodes the parameters and processes them into exercise-related data that may be provided to the user in order provide the user with information related to an exercise or to control the execution of the exercise. To enable the irregular transmission/reception timings, the reception control circuitry 109 may be configured to cause the short range receiver 108 to receive short range signals asynchronously, e.g. the short range receiver may constantly monitor for the short range signals. The same analogy applies when the transmitter apparatus is comprised in a stride sensor comprising an acceleration sensor and the measurement processing circuitry. The transmission of the short range signal from the stride sensor to the receiver apparatus may be triggered by the detection of a determined event in the measured acceleration information, e.g. detection of a determined acceleration waveform arising from a step, for example. With respect to other measurement devices, e.g. a positioning device, the short range transmissions may be pseudo-randomized in time on the basis of a determined random or pseudo-random sequence defining transmission timings for the short range transmissions.

In an embodiment, the short-range signal is a measurement signal carrying information on the measurement. The short range signal may be transmitted upon detection of the determined event in the measurement and, thus, the reception of the short range signal indicates, in addition to the radio resource, occurrence of the event in the measurement. For example, the receiver apparatus may compute RR intervals from time duration between reception timings of consecutive short range signal pulses.

Figure 4:
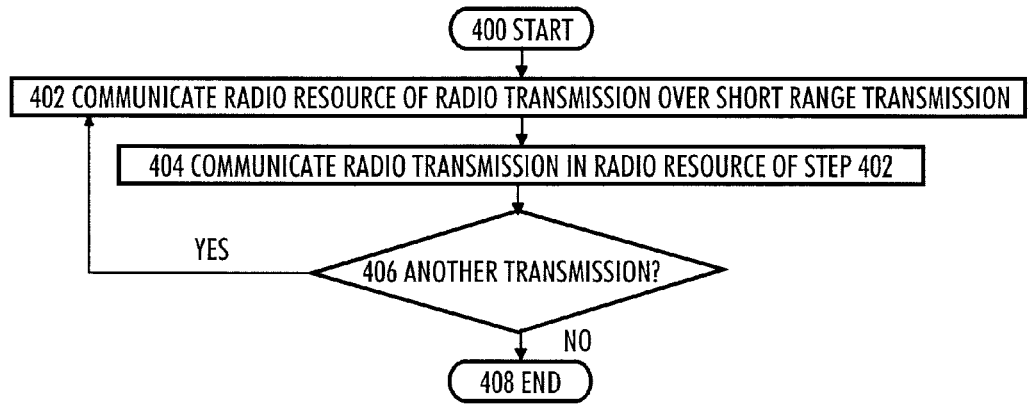
FIG. 4 is a flow diagram of a process for carrying out wireless communication according to an embodiment of the invention.

Let us now consider a general wireless communication procedure according to an embodiment of the invention with respect to a flow diagram of FIG. 4. The process may be carried out in a wireless communication apparatus, e.g. above-mentioned transmitter or receiver apparatus. The process is started in block 400. In block 402, communication of a short-range signal indicating a radio resource used for transmission of a radio signal is triggered. When the wireless communication apparatus carrying out the process is the transmitter apparatus 100, 202, block 402 includes transmission of the short range signal. On the other hand, when the wireless communication apparatus carrying out the process is the receiver apparatus 106, 204, block 402 includes reception of the short range signal. By definition, the radio signal has a longer wireless communication range than the wireless communication range of the short-range signal. In block 404, communication of the radio signal in the radio resource indicated with the short-range signal is triggered. When the wireless communication apparatus carrying out the process is the transmitter apparatus 100, 202, block 404 includes transmission of the radio signal. On the other hand, when the wireless communication apparatus carrying out the process is the receiver apparatus 106, 204, block 402 includes reception of the radio signal. In block 406, it is determined whether or not to carry out another transmission. With respect to the transmitter apparatus 100, 202, the determination may be based on at least one of the following: availability of transmission data in transmission buffers, whether or not to attempt to pair with the receiver apparatus, and disconnection in the paired connection. With respect to the transmitter apparatus, the determination may be based on the decision, whether or not to configure the short range receiver for reception of the short range signals. The decision may be based on at least one of (un)successful pairing, and disconnection of the paired connection. If it is determined in block 406 that another transmission is to be carried out, the process returns to block 402. On the other hand, if it is determined in block 406 that another transmission is not to be carried out, the process ends in block 408. The termination of the process may include switching off the short range transmitter/receiver and/or switching off both short range and radio transmitters/receivers.

The process of FIG. 4 may be carried out in the communication control circuitry 103, 109 of the wireless communication device 100, 202, 106, 204 according to an embodiment of the invention. The process may be defined by a computer program product stored in a computer-readable medium. The transmission medium may be a transitory or a non-transitory transmission medium. The computer program may be in source code form, object code form, or in some intermediate form. The computer-readable medium may be a carrier which may be any entity or device capable of carrying the program. Such carriers include a record medium, computer memory, read-only memory, electrical carrier signal, telecommunications signal, and software distribution package, for example. Depending on the processing power needed, the computer program may be executed in a single electronic digital processing unit or it may be distributed amongst a number of processing units.

As used in this application, the term 'circuitry' refers to all of the following: (a) hardware-only circuit implementations, such as implementations in only analog and/or digital circuitry, and (b) to combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) to circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term "circuitry" would also cover an implementation of merely a processor (or multiple processors) or portion of a processor and its (or their) accompanying software and/or firmware. The term "circuitry" would also cover, for example and if applicable to the particular element, a baseband integrated circuit or applications processor integrated circuit for a mobile phone or a similar integrated circuit in server, a cellular network device, or other network device.

It will be obvious to a person skilled in the art that, as technology advances, the inventive concept can be implemented in various ways. The invention and its embodiments are not limited to the examples described above but may vary within the scope of the claims.

What is claimed is:

1. An apparatus comprising:
    a transmission control circuitry configured to control a short-range transmitter; and
    a radio transmitter operationally connectable to the transmission control circuitry, the radio transmitter having a longer wireless transmission range than a wireless transmission range of the short-range transmitter, wherein the transmission control circuitry is configured to cause the short-range transmitter to transmit a short-range signal indicating to a receiver apparatus receiving the short-range signal a radio resource used for transmission of a radio signal, and to cause the radio transmitter to transmit the radio signal in the radio resource indicated with the short-range signal, wherein the radio resource indicated with the short-range signal is a transmission timing of the radio signal, wherein the transmission control circuitry is arranged to cause the transmission of the radio signal at the transmission timing indicated in the short-range signal.

2. The apparatus of claim 1, wherein a transmission timing of the short-range signal indicates the transmission timing of the radio signal.

3. The apparatus of claim 2, wherein there is fixed time interval between the transmission timing of the short-range signal and the transmission timing of the radio signal.

4. The apparatus of claim 1, wherein the short-range signal is a measurement signal carrying information on a measurement, and wherein the apparatus further comprises a measurement processing circuitry configured to execute measurement signal processing at irregular time intervals, wherein the execution of the measurement causes the measurement processing circuitry to generate measurement data which triggers said transmission of the short-range signal, thereby causing irregular transmission timings for said short-range signals.

5. The apparatus of claim 4, wherein the measurement signal is a heart-rate signal and wherein the transmitter apparatus is a heart-rate transmitter.

6. The apparatus of claim 1, wherein the radio signal carries an identification code that identifies the radio transmitter and that is used for initiating a pairing protocol for a radio connection, and wherein the transmission control circuitry is configured to control the radio transmitter to initiate the pairing protocol with a radio receiver apparatus after transmitting the identification code.

7. An apparatus comprising:
    a transmission control circuitry configured to control a short-range transmitter; and
    a radio transmitter operationally connectable to the transmission control circuitry, the radio transmitter having a longer wireless transmission range than a wireless transmission range of the short-range transmitter, wherein the transmission control circuitry is configured to cause the short-range transmitter to transmit a short-range signal indicating to a receiver apparatus receiving the short-range signal a radio resource used for transmission of a radio signal, and to cause the radio transmitter to transmit the radio signal in the radio resource indicated with the short-range signal, wherein the short-range transmitter is an induction-based transmitter and the short range signal is a magnetic signal.

8. A method, comprising:
    causing, in a wireless communication apparatus, communication of a short-range signal indicating a radio resource used for transmission of a radio signal, wherein the radio signal has a longer wireless communication range than a wireless communication range of the short-range signal, and
    causing, in the wireless communication apparatus, communication of the radio signal in the radio resource indicated with the short-range signal, wherein the radio resource indicated with the short-range signal is a communication timing of the radio signal, wherein the wireless communication apparatus is arranged to cause the communication of the radio signal at the communication timing indicated in the short-range signal.

9. A computer program product embodied on a non-transitory distribution medium readable by a computer and comprising program instructions which, when executed by the computer, perform a computer process comprising:
    causing, in a wireless communication apparatus, communication of a short-range signal indicating a radio resource used for transmission of a radio signal, wherein the radio signal has a longer wireless communication range than a wireless communication range of the short-range signal, and
    causing, in the wireless communication apparatus, communication of the radio signal in the radio resource indicated with the short-range signal, wherein the radio resource indicated with the short-range signal is a communication timing of the radio signal, wherein the wireless communication apparatus is arranged to cause the communication of the radio signal at the communication timing indicated in the short-range signal.

10. An apparatus comprising:
    a reception control circuitry configured to control a short-range receiver and a radio receiver both operationally connectable to the reception control circuitry, wherein the reception control circuitry is configured to detect reception of a short-range signal in the short-range receiver, to determine from the received short-range signal a radio resource of a radio signal, and to cause the radio receiver to receive the radio signal in the radio resource determined from the short-range signal and to decode data carried by received radio signal, wherein the radio resource indicated with the short-range signal is a transmission timing of the radio signal, wherein the reception control circuitry is arranged to cause the reception of the radio signal at the transmission timing indicated in the short-range signal.

11. The apparatus of claim 10, wherein the radio resource indicated with the short-range signal is a reception timing of the radio signal, and the reception control circuitry is arranged to synchronize the radio reception circuitry to receive the radio signal at the reception timing determined from the received short-range signal.

12. The apparatus of claim 11, wherein the reception timing of the short-range signal indicates the reception timing of the radio signal.

13. The apparatus of claim 10, wherein the short-range signal is a measurement signal carrying information on a measurement, and the reception control circuitry is arranged to receive short range signals at irregular time intervals.

14. The apparatus of claim 13, wherein the measurement signal is a heart-rate signal and the receiver apparatus is an exercise apparatus configured to process the measurement signal and to provide information on an exercise on the basis of the processed measurement signal.

15. The apparatus of claim 10, wherein the radio signal carries an identification code that identifies a radio transmitter that transmitted the radio signal, and the reception control circuitry is arranged to identify the radio transmitter from the identification code received in the radio signal associated with the radio resource indicated by the received short range signal and to configure the radio receiver to execute a pairing protocol for a radio connection with said radio transmitter.

16. An apparatus comprising:
a reception control circuitry configured to control a short-range receiver and a radio receiver both operationally connectable to the reception control circuitry, wherein the reception control circuitry is configured to detect reception of a short-range signal in the short-range receiver, to determine from the received short-range signal a radio resource of a radio signal, and to cause the radio receiver to receive the radio signal in the radio resource determined from the short-range signal and to decode data carried by received radio signal, wherein the short-range receiver is an induction-based receiver and the short range signal is a magnetic signal.

17. The apparatus of claim 10, wherein the reception control circuitry is arranged to compare a reception timing of a radio signal received through the radio receiver with a reception timing of the short-range signal and to decode the radio signal, if the reception timing of the radio signal relative to the reception timing of the short-range signal matches with a predetermined timing relation.

18. A method, comprising:
causing, in a short-range transmitter of a wireless communication apparatus, communication of a short-range signal indicating a radio resource used for transmission of a radio signal, wherein the radio signal has a longer wireless communication range than a wireless communication range of the short-range signal, and
causing, in the wireless communication apparatus, communication of the radio signal in the radio resource indicated with the short-range signal, wherein the short-range transmitter is an induction-based transmitter and the short range signal is a magnetic signal.

19. A computer program product embodied on a non-transitory distribution medium readable by a computer and comprising program instructions which, when executed by the computer, perform a computer process comprising:
causing, in a short range transmitter of a wireless communication apparatus, communication of a short-range signal indicating a radio resource used for transmission of a radio signal, wherein the radio signal has a longer wireless communication range than a wireless communication range of the short-range signal, and
causing, in the wireless communication apparatus, communication of the radio signal in the radio resource indicated with the short-range signal, wherein the short-range transmitter is an induction-based transmitter and the short range signal is a magnetic signal.

* * * * *